United States Patent [19]

Enloe

[11] Patent Number: 4,685,916

[45] Date of Patent: Aug. 11, 1987

[54] ELASTIC WAIST FOR DISPOSABLE ABSORBENT GARMENT

[75] Inventor: Kenneth M. Enloe, Neenah, Wis.

[73] Assignee: Kimberly-Clark Corporation, Neenah, Wis.

[21] Appl. No.: 837,475

[22] Filed: Mar. 7, 1986

[51] Int. Cl.[4] ............................................. A61F 13/16
[52] U.S. Cl. ............................ 604/385 A; 604/385 R
[58] Field of Search ................. 604/358, 378, 385.1, 604/385.2

[56] References Cited

U.S. PATENT DOCUMENTS

| | | | |
|---|---|---|---|
| 2,841,147 | 7/1958 | McLaurin | 604/358 |
| 3,756,878 | 9/1973 | Willot | 604/358 |
| 3,990,450 | 11/1976 | Schaar . | |
| 4,300,562 | 11/1981 | Pieniak | 604/385.2 |
| 4,324,245 | 4/1982 | Mesek et al. . | |
| 4,381,781 | 5/1983 | Sciaraffa et al. | 604/372 |
| 4,388,075 | 6/1983 | Mesek et al. | 604/385 |
| 4,430,086 | 2/1984 | Repke | 604/385 |
| 4,515,595 | 5/1985 | Kievit et al. | 604/385 |

*Primary Examiner*—Stephen C. Pellegrino
*Assistant Examiner*—Denise Whelton
*Attorney, Agent, or Firm*—Paul Yee

[57] ABSTRACT

An improved disposable absorbent garment includes a covering sheet member having a waistband section at each longitudinal end thereof and an intermediate section interconnecting the waistband sections. An absorbent body is superposed in facing relation on the covering sheet member, and has a notch section formed into at least one terminal, longitudinal edge thereof. An elastomeric member is attached to at least one of the covering sheet member waistband sections adjacent to the absorbent body notch section for shirring the waistband of the garment.

23 Claims, 5 Drawing Figures

ELASTIC WAIST FOR DISPOSABLE ABSORBENT GARMENT

FIELD OF THE INVENTION

The present invention relates to disposable absorbent garments having elasticized waistbands. More particularly, the present invention relates to an absorbent garment having an improved elastic waist which provides improved appearance and functionality.

BACKGROUND OF THE INVENTION

Disposable absorbent garments, such as diapers, incontinence garments, and the like, have become popular because of their effectiveness in absorbing body exudates and because of their convenience. To improve the appearance and to reduce leakage from the waistband sections of such absorbent garments, elastic strips have been incorporated into the garment to produce gathered, snug fitting waistbands.

In particular, U. S. Pat. No. 4,381,781 issued May 3, 1983 to M. Sciaraffa, et al. describes an elasticized waist diaper in which a layer of elastic material is positioned in an opening in the waist area of the diaper. The elastic layer is located such that it forms a portion of the waist edge of the diaper.

Other diaper configurations have been developed to incorporate elasticized, gathered waistbands. Representative examples of such diapers are shown in U.S. Pat. No. 3,990,450 issued Nov. 9, 1976 to C. Schaar; U.S. Pat. No. 4,324,245 issued April 13, 1982 to F. Mesek, et al.; U.S. Pat. No. 4,388,075 issued June 14, 1983 to F. Mesek, et al.; and U.S. Pat. No. 4,430,086 issued Feb. 7, 1984 to V. Repke.

Conventional elastic waistband configurations for disposable absorbent garments, however, have not been completely satisfactory because the waistbands have tended to sag and curl over toward the inside or outside of the garment. This can reduce the effectiveness of the elastic waist and can create an unsightly appearance.

To address the problems of waistband curl over and unsightly appearance, U.S. Pat. No. 4,515,595 issued May 7, 1985 to Kievit, et al. describes a diaper employing a configuration in which the waistbands are formed by affixing elastic elements between the diaper topsheet and backsheet using regularly spaced, transversely extending regions of securement. Regions of nonsecurement are formed between pairs of the regions of securement thereby forming channels which allow the diaper to breath and also form corrugations which tend to inhibit waistband roll over. The diaper design taught by Kievit, et al., however, is relatively complex and costly to manufacture. As a result, there has been a continued need for an economical and efficient construction for reducing the undesired roll over of the elasticized waistbands in disposable absorbent garments.

BRIEF DESCRIPTION OF THE INVENTION

The present invention provides an improved disposable absorbent garment which includes a covering sheet member having a waistband section at each longitudinal end thereof and an intermediate section which interconnects the waistband sections. An absorbent body is superposed in facing relation with the covering sheet and has a notch section formed into at least one terminal, longitudinal edge thereof. An elastomeric means is attached to at least one of the covering sheet member waistband sections adjacent the absorbent body notch section for shirring a portion of the garment waistband. In addition, preferred configurations of the invention include securing means connected to the backsheet for holding the garment on a wearer.

The absorbent garment of the present invention can advantageously reduce waistband sag and roll over without employing a complex structure for the waist elastic attachment. The diaper design provided by the invention can also reinforce and support the attachment zones employed by the garment securing means. In addition, the garment design can advantageously improve the waist fit and appearance and can reduce the likelihood of leakage past the waist section of the garment.

BRIEF DESCRIPTION OF THE DRAWINGS

The present invention will be more fully understood and further advantages will become apparent when reference is made to the following detailed description of the invention and the drawings in which.

DETAILED DESCRIPTION OF THE INVENTION

The following detailed description of the invention will be made in the context of a disposable diaper garment. It will be readily appreciated, however, that other disposable absorbent garments, such as incontinence garments and the like, may also be constructed employing the present invention.

Figure 1:
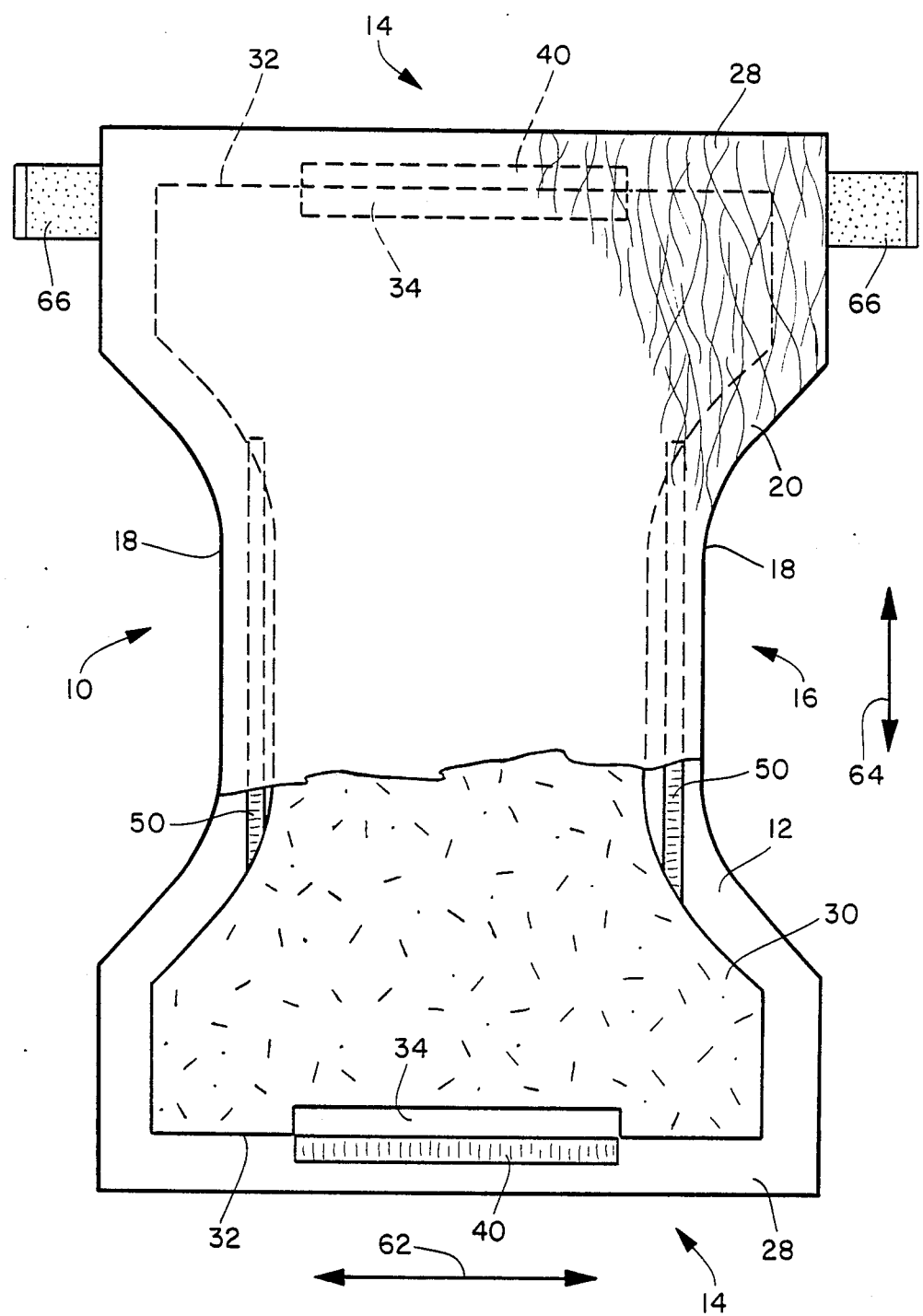
FIG. 1 representatively shows a plan view of a disposable diaper garment wherein a portion of the liner sheet is cut away for clarity.
Figure 2:
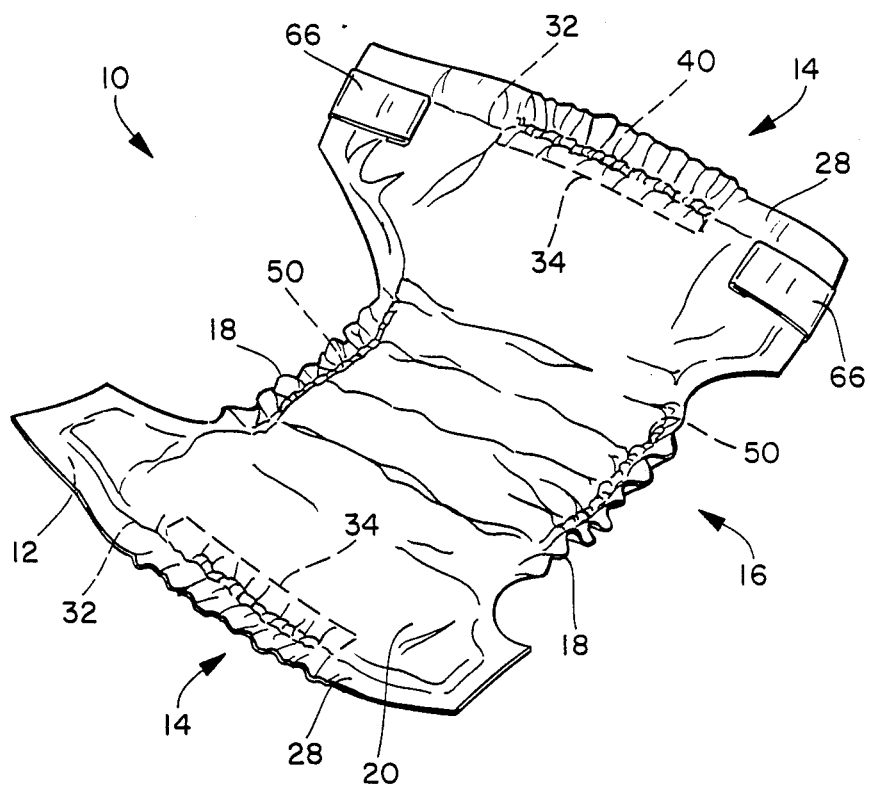
FIG. 2 representatively shows a plan view of a diaper garment in which the elastic has contracted to form elasticized gathers at the legband sections and the waistband sections.

Referring to FIGS. 1 and 2, a representative disposable diaper 10 constructed in accordance with the present invention includes a covering sheet member, such as the sheet comprising liner sheet 20 and backsheet 12. The covering sheet member has a waistband section 14 at each longitudinal end thereof and an intermediate section 16 interconnecting the two waistband sections. This intermediate section, in turn, comprises a crotch portion which is constructed and configured for placement in between the legs of the wearer. An absorbent body 30 is superposed in facing relation with backsheet 12 and is located between the backsheet and liner sheet 20. The absorbent body also has a notch section 34 formed into at least one terminal, longitudinal edge 32 thereof. An elastomeric member 40 is attached to at least one of the covering sheet waistband sections adjacent to the absorbent body notch section 34 for shirring the waistband of the garment. Securing means, such as pressure-sensitive adhesive tape fasteners 66, are connected to backsheet 12 and are configured to hold the garment on the wearer. In particular, tape fasteners 66 are employed to secure the two waistband sections 14 of the diaper about the waist of an infant. Diaper 10 may also include elasticized legbands to improve the fit of the diaper around the legs of the infant and to reduce the leakage of liquids from the diaper crotch section. The elastic bands are provided by elastomeric strip members 50 located adjacent to the absorbent body 30 along each of the marginal side edges 18 of the diaper.

Figure 3:
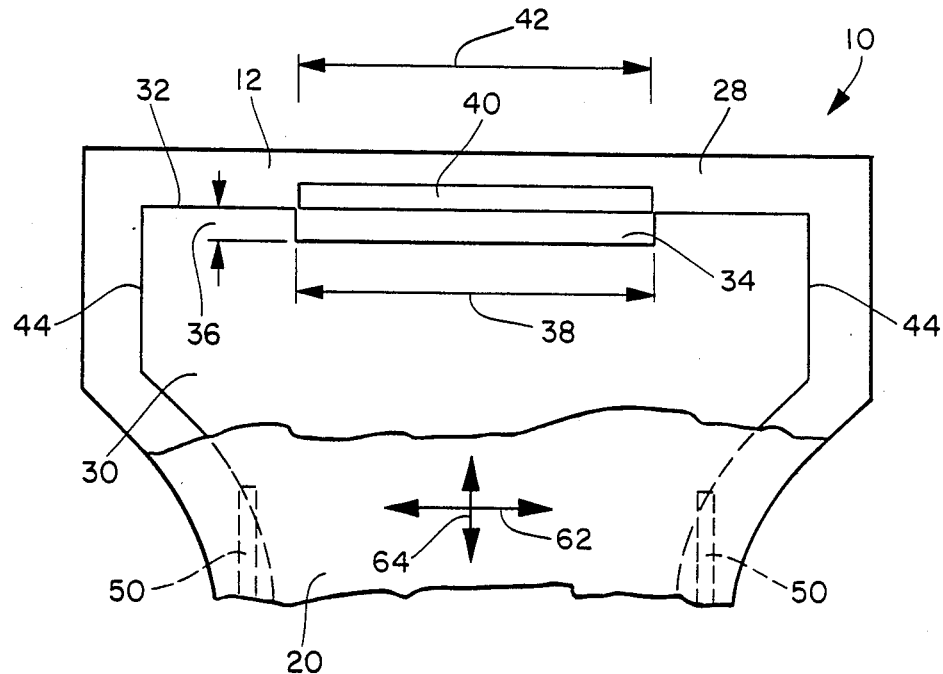
FIG. 3 representatively shows a more detailed, plan view of the notched absorbent at the diaper waistband and the elastic element employed to gather the waistband.

Diaper 10 can be rectangular shaped, but preferably has a "hour-glass" shape or a I-shape, as representatively shown in FIG. 3. As a result, the diaper delimits waistband sections at each of its two longitudinal ends and an intermediate section which defines a generally narrower crotch section and which interconnects the two waistband sections. These diaper waistband and intermediate sections substantially correspond to the waistband and intermediate sections of backsheet 12. During use, the two waistband sections effectively encircle the waist of the wearer, with one waistband section spanning across the "front" side of the wearer and the other waistband section spanning across the "rear" or back side of the wearer. The ear-like flaps at the lateral side edges of the waistband sections would then overlap at the sides of the wearer and would be secured with tape fasteners 66. A portion of the diaper intermediate section passes between the legs and covers the crotch of the wearer.

Backsheet member 12 is preferably composed of a liquid impermeable material, such as a polyolefin sheet film material. For example, suitable polyolefin films include polyethylene and polypropylene films. The liquid impermeable characteristic of backsheet 12 substantially prevents the undesired migration of absorbed fluids from diaper 10 to the outer clothes of the wearer.

Absorbent body 30 generally comprises an absorbent pad and may include one or more layers of tissue wrap. Absorbent body 30 is typically composed of conventional absorbent materials, such as creped tissue wadding or airlaid cellulosic fibers. Such airlaid cellulosic fibers are commonly referred to as "fluff". The absorbent body can also include selected quantities of hydrogel superabsorbent materials. Such superabsorbent materials include inorganic or organic compounds capable of absorbing aqueous fluids and retaining them under moderate pressures. For good results, the hydrogels must be water insoluble. Examples are inorganic materials, such as silica gels, and organic compounds, such as cross-linked polymers. Cross-linking may be by covalent, ionic, vander Waals, or hydrogen bonding. Examples of polymers include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, polyacrylates, and isobutylene maleic anhydride copolymers, and mixtures therof.

In the illustrated embodiment, absorbent body 30 delimits two waistband sections, one at each longitudinal end thereof. In addition, the absorbent body delimits an intermediate section which interconnects the two waistband sections and includes a generally narrower crotch section. Absorbent body 30 is assembled in a superposed, facing relation onto backsheet 12 employing conventional fastening means, such as sonic bonds, thermal bonds or adhesive bonds or the like. For example, in the shown embodiment, lines of hot melt, pressure-sensitive adhesive are employed to bond absorbent body 30 onto backsheet 12. The absorbent body is generally configured to be smaller than backsheet 12. As a result, the side margins of backsheet 12 extend beyond the lateral side edges of absorbent body 30, and the longitudinal end margins of the backsheet extend beyond the longitudinal ends of the absorbent body.

Liner 20 in the illustrated embodiment is composed of a porous, nonwoven material, such as a spunbond material composed of polyolefin filaments. Suitable filaments for the spunbond material include, for example, polyethylene and polypropylene filaments. The liner sheet is a liquid permeable material configured to allow the passage of liquids therethrough. As a result, the liner helps maintain a dry, soft surface next to the skin of the wearer. Liner 20 is generally coterminous with backsheet 12, and is attached in a superposed, facing relation onto absorbent body 30 with suitable bonding means, such as a hot melt adhesive The liner is also bonded to backsheet 12 along the contacting portions of the side margins and end margins of the liner and backsheet. As can be seen from the Figures, liner 20 has a configuration similar to that of backsheet 12, and includes a waistband section at each longitudinal end thereof and an intermediate section. The intermediate section interconnects the two liner waistband sections and defines a narrow crotch section.

Figure 4:
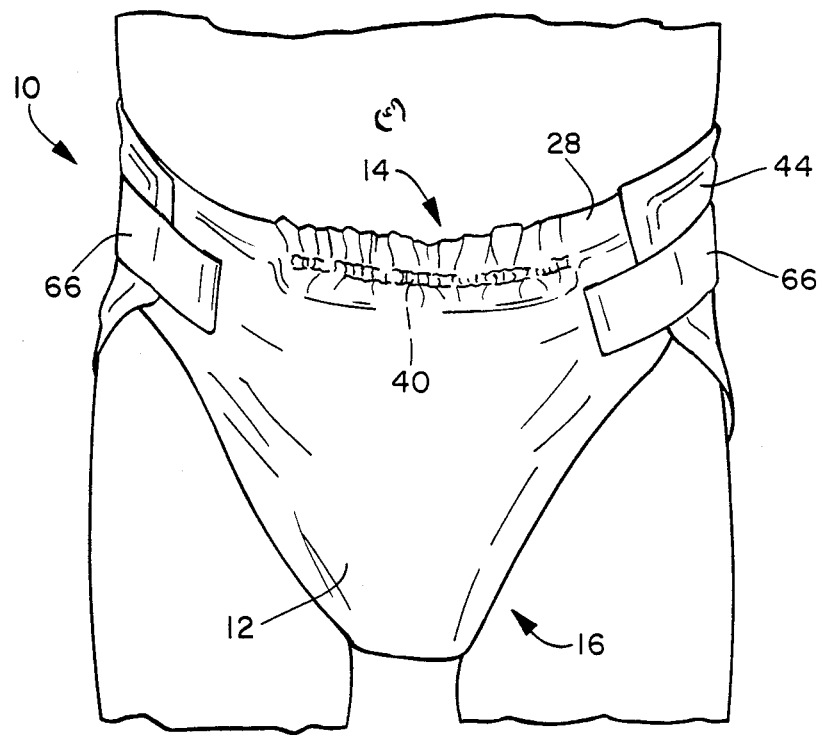
FIG. 4 representatively shows a perspective view of an infant wearing a garment having the gathered waistband and the notched absorbent pad.

Referring now to FIGS. 3 and 4, the longitudinal ends of absorbent body 30 include absorbent ears 44 which extend into the waistband sections of diaper 10. Absorbent body 30 also includes a recess or notch 34 formed into at least one longitudinal edge of the absorbent pad. In particular aspects of the invention, both the "front" and "rear" waistband sections of diaper 10 are elasticized, and notches 34 are formed in both the front and rear waistband sections of the absorbent pad. For the purposes of simplicity, FIGS. 3 and 4 illustrate a single "front" waistband section. However, it will be readily apparent that the "rear" waistband section at the opposite end of the diaper garment can have a similar or different arrangement and construction, as desired.

Figure 5:
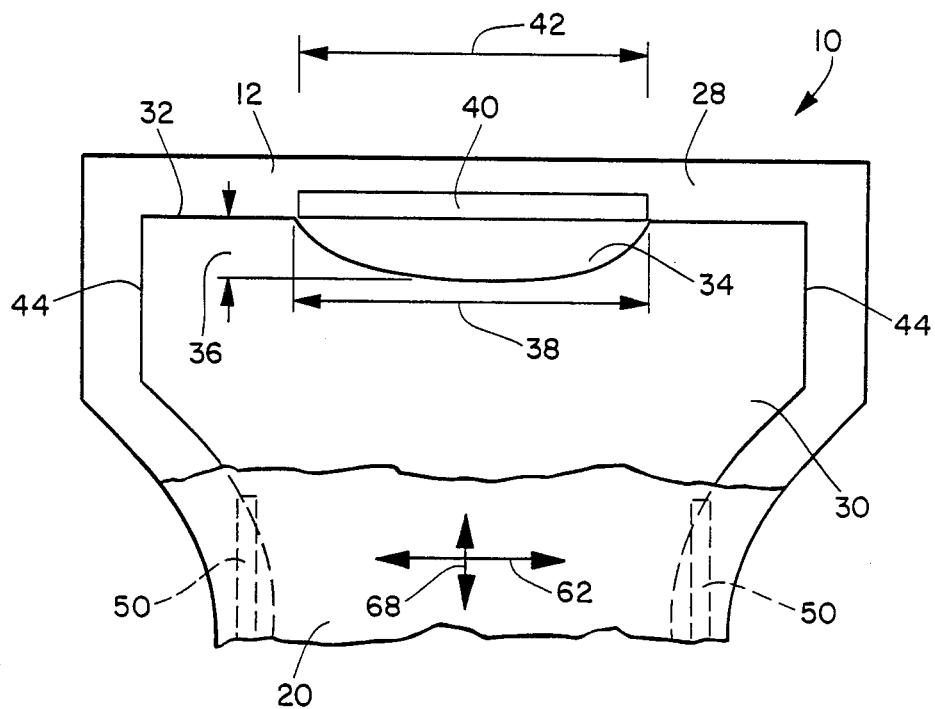
FIG. 5 representatively shows a portion of an absorbent pad having an arcuate shaped notch formed therein.

Notch 34 may have a rectilinear shape, as representatively shown in FIG. 3, or may have an arcuate, curvilinear shaped outline, as representatively shown in FIG. 5. In particular aspects of the invention, the notch is centrally positioned with respect to the diaper cross-direction, and the maximum depth 36 of notch 34 ranges from about 0.5-2.0 inches (1.27-5.08cm). In addition, the length 38 of notch 34 along the crosswise direction 62 of diaper 10 is at least about 20% of the cross-directional width of the absorbent body waistband section. Preferably, notch 34 has a spanning length which is within about 30-60% of the cross-directional width of the absorbent body waistband section to provide improved effectiveness.

Notch 34 may be formed into absorbent body 30 employing various conventional manufacturing techniques. For example, the notch may be directly and simultaneously formed during the process of airlaying the cellulosic fibers employed to form the absorbent pad portion of absorbent body 30. Alternatively, the notch can be cut out from the absorbent pad after the absorbent pad has been formed. Conventional devices, such as die cutters, can be employed to cut the pad.

The illustrated embodiments of the invention show a single notch formed in the longitudinal edge of the absorbent body. However, it will be readily apparent that a plurality of component notches may be substituted for the single notch shown. Preferably, each of the component notches would have side edges bounded by absorbent material that extends longitudinally toward the end margins 28 of the garment to help stiffen the end margin regions and reduce waistband roll over.

As previously mentioned, the front and rear waistband sections of the absorbent body may have differently configured notches formed therein. In a particular aspect of the invention, the front waistband section includes a rectangular shaped notch and the rear waistband section includes an arcuate, crescent shaped notch. This configuration can provide a better fit on an infant because the front portion of the infant's waist is generally convex and the rear portion of the infant's waist is generally concave.

In the illustrated embodiment, the ears 44 of absorbent body 30 extend both laterally in the diaper cross direction 62 and longitudinally along direction 64 toward the terminal ends of diaper 10. As a result of its longitudinal extent, the absorbent material of absorbent body 30 fills a greater proportion of the longitudinal end margins 28 of the diaper at side edges of notch 34. The presence of this absorbent material stiffens the lateral portions of the diaper waistband that extend toward the ear sections and provides a larger and firmer landing attachment zone for fastener tapes 66. The relatively greater firmness provided by the presence of absorbent material also helps to support and stiffen the waistband portions that are located proximate to the terminal ends of waist elastic strips 40. As a result, the distinctive waistband configuration can help to reduce the likelihood that the elasticized portions of the waistband section will curl and roll over toward the body of the wearer.

The longitudinal extent of the absorbent material also encourages the securement of adhesive tapes 66 closer to the longitudinal edges of the diaper. As a result, the tension exerted by the tape fasteners is located closer to and more in alignment with the terminal, horizontal edges of the waistband sections. This arrangement of the tape tabs can further help reduce the likelihood of waistband roll over.

As previously mentioned, absorbent body 30 may also include one or more layers of tissue wrap to increase the integrity of the absorbent body. This tissue wrap material may or may not be notched in conformance with the notch formed in the main absorbent pad. If the tissue wrap material is not notched, the tissue may extend into the notch area 34. Typically, however, the tissue wrap layers are sufficiently flexible such that they do not provide excessive resistance to the shirring and gathering action produced by the waist elastic strips 40.

Elastic strips 40 provide a waist elastic means which operably gathers and shirs the end margins 28 of the diaper waistband sections. Typically, elastic strips 40 are adhesively attached to the diaper end margins while the strips are in an oriented, elongated state. After the strips are assembled to the diaper end margins, the strips are activated, such as by the application of heat, to cause the strips to contract from their elongated state to a shorter, elasticized state. This contraction shirs the garment end margin and provides an elasticized waistband. The illustrated embodiment shows elastic strips 40 attached only to backsheet 12. However, in alternative embodiments of the invention, elastic strips 40 may be attached only to liner 20, or attached to both the backsheet and liner.

Various types of heat activatable elastic materials may be employed in the present invention. For example, a suitable material is Coban material No. KER 2207 or 2210, an elasticizable material manufactured by 3M Corporation, St. Paul, MN. This material includes elastic strands held in a stretched state by a rigid substrate that is bonded to the elastic strands. The application of heat weakens the substrate and allows the elastic strands to contract and shir the selected garment portions to which the elasticizable material is attached.

To form the improved elasticized waistband of the invention, waist elastic strip 40 is secured at a position which is within notch 34 or closely adjacent to the notch. If strip 40 is located outside of notch 34, the inner most edge of the elastic strip is preferably located within about 1 cm of the open end of the notch to provide the desired effectiveness. In the illustrated embodiment of the invention, the waist elastic strip is approximately coterminous with the lateral side edges of notch 34. If desired, however, length 42 of elastic strip 40 may extend past or stop short of the side edges of the notch by a selected distance and still provide the desired effectiveness.

The combination of waist elastic 40 and notch 34 advantageously provides a configuration wherein the portions of the backsheet and liner sheet material within the region bounded by notch 34 are more readily shirred by elastic strip 40. The stiffer, firmer waistband regions located outside of notch 34 are more resistant to the shirring effect. As a result, the elasticized section of the waistband tends to tuck or curl inwardly toward the body of the wearer is effectively inhibited by the stiffer waistband portions which border notch 34. Since the distinctive configuration of the invention advantageously limits the tendency of the waistband to curl and roll over, the improved waistband of the invention maintains a better fit against the body and presents a more pleasing appearance.

In the shown embodiment, waist elastic strips 40 have a substantially linear, straight-line configuration. It should be readily apparent, however, that curvilinear configurations of the elastic strips may also be employed. Such curvilinear configurations of the waist elastic strips are contemplated as being within the scope of the present invention.

To further improve the performance of diaper garment 10, leg elastic means, such as elastic strips 50 are located adjacent to absorbent body 30 at the side margins of backsheet 12 and liner 20. The leg elastics are adhesively bonded to at least the backsheet 12, and in certain configurations, are bonded to both backsheet 12 and liner 20. In conventional manufacturing processes, the leg elastics are attached while they are held in a stretched condition. After assembly, the tension in the elastic strips 50 is released. The elastic strips then contract to shir and gather the diaper side margins to form the elasticized legbands. These gathered legbands effectively form elasticized gaskets that reduce the leakage of fluids past the edges of the diaper crotch section.

Having thus described the invention in rather full detail, it will be readily apparent to a person having ordinary skill in the art that various changes and modifications can be made without departing from the spirit of the invention. All of such changes and modifications are contemplated as being within the scope of the invention as defined by the subjoined claims.

What is claimed is:

1. A disposable absorbent garment, comprising:
   a. a covering sheet member having a waistband section at each longitudinal end thereof and an intermediate section interconnecting said waistband sections;
   b. an absorbent body superposed in facing relation with said covering sheet member and having a notch section formed in at least one terminal, longitudinal edge thereof, said notch forming a recess having side edges which extend longitudinally toward an end margin of the garment; and
   c. an elastomeric member attached to at least one of said covering sheet member waistband sections adjacent to said absorbent body notch section for shirring a waistband of said garment.

2. A garment as recited in claim 1, further comprising securing means connected to said covering sheet member for holding said garment on a wearer.

3. A garment as recited in claim 2, wherein said covering sheet member comprises:
   a substantially liquid impermeable backsheet; and
   a substantially liquid permeable liner sheet which is superposed in facing relation with said backsheet and said absorbent body with the absorbent body located between said backsheet and said liner sheet.

4. A garment as recited in claim 1, wherein said notch has a depth which ranges from about 1.27–5.08cm.

5. A garment as recited in claim 1, wherein said notch has a length along the cross-direction of the garment which is at least about 20% of the cross-directional length of the absorbent body waistband section.

6. A garment as recited in claim 1, wherein said notch has a length along the cross-direction of the garment which ranges from about 30–60% of the cross-directional length of the absorbent body waistband section.

7. A garment as recited in claim 1, wherein said notch is rectlinear in shape.

8. A garment as recited in claim 1, wherein said notch has a curvilinear shaped outline.

9. A disposasble absorbent garment, comprising:
   a. a substantially liquid impermeable backsheet having a waistband section at each longitudinal end thereof and an intermediate section interconnecting said waistband sections;
   b. a substantially liquid permeable liner sheet which is superposed in facing relation with said backsheet;
   c. an absorbent body located between said backsheet and said liner sheet and having a notch section formed in at least one terminal, longitudinal edge thereof, said notch forming a recess having side edges which extend longitudinally toward an end margin of the garment;
   d. an elastomeric member attached to at least one of said backsheet waistband sections adjacent to said absorbent body notch section for shirring a waistband of said garment; and
   e. securing means connected to said backsheet for holding said garment on a wearer.

10. A garment as recited in claim 9, wherein said notch has a depth which ranges from about 1.27–5.08cm.

11. A garment as recited in claim 9, wherein said notch has a length along the cross-direction of the garment which is at least about 20% of the cross-directional length of the absorbent body waistband section.

12. A garment as recited in claim 9, wherein said notch has a length along the cross-direction of the garment which ranges from about 30–60% of the cross-directional length of the absorbent body waistband section.

13. A garment as recited in clasim 9, wherein said notch is rectlinear in shape.

14. A garment as recited in claim 9, wherein said notch has a curvilinear shaped outline.

15. A disposable absorbent garment, comprising:
   a. a substantially liquid impermeable backsheet having a waistband section at each longitudinal end thereof and an intermediate section interconnecting said waistband sections;
   b. a substantially liquid permeable liner sheet which is superposed in facing relation on said backsheet, and which has a waistband section at each longitudinal end thereof and an intermediate section interconnecting said waistband sections;
   c. an absorbent body located between said backsheet and said liner sheet, said absorbent body having a waistband section at each longitudinal end thereof, an intermediate section interconnecting said waistband sections, and having a centrally positioned notch section formed in at least one terminal longitudinal edge thereof, saidnotch forming a recess having side edges which extend longitudinally toward an end margin of the garment;
   d. an elastomeric member attached to at least one of said backsheet and liner sheet waistband sections adjacent to said absorbent body notch section for shirring the waistband of said garment; and
   e. securing means connected to said backsheet for holding said garment on a wearer.

16. A garment as recited in claim 15, wherein said notch has a depth which ranges from asbout 1.27–5.08cm.

17. A garment as recited in claim 15, wherein said notch has a length along the cross-direction of the garment which is at least about 20% of the cross-directional length of the absorbent body waistband section.

18. A garment as recited in claim 15, wherein said notch has a length along the cross-direction of the garment which ranges from about 30–60% of the cross-directional length of the absorbent body waistband section.

19. A garment as recited in claim 15, wherein said notch is rectlinear in shape.

20. A garment is recited in claim 15, wherein said notch has a curvilinear shaped outline.

21. A garment as recited in claim 1, wherein said notch section forms a plurality of recesses having side edges which extend longitudinally toward the end margin of the garment.

22. A garment as recited in claim 9, wherein said notch section forms a plurality of recesses having side edges which extend longitudinally toward the end margin of the garment.

23. A garment as recited in claim 15, wherein said notch section forms a pllurallity of recesses having side edges which extend longitudinally toward the end margin of the garment.

* * * * *